United States Patent [19]
Goldstein et al.

[11] Patent Number: 6,054,116
[45] Date of Patent: Apr. 25, 2000

[54] CHIMERIC MOUSE FOR HUMAN AND MOUSE IMMUNE SYSTEMS

[75] Inventors: Harris Goldstein; Tobias R. Kollmann, both of Bronx, N.Y.

[73] Assignee: Albert Einstein College of Medicine of Yeshiva University, Bronx, N.Y.

[21] Appl. No.: 09/115,424

[22] Filed: Jul. 15, 1998

Related U.S. Application Data

[62] Division of application No. 08/739,281, Oct. 29, 1996, Pat. No. 5,811,635, which is a continuation of application No. 08/309,563, Sep. 20, 1994, abandoned, which is a continuation of application No. 07/924,348, Aug. 3, 1992, abandoned.

[51] Int. Cl.⁷ .............................. C12N 5/10; A61K 49/00
[52] U.S. Cl. ................................. 424/9.2; 800/8; 800/9; 800/11; 424/9.1
[58] Field of Search ...................... 800/8, 9, 11; 424/9.1, 424/9.2; 435/375

[56] References Cited

PUBLICATIONS

"Development of Multiple Organ–Localized Autoimmune Diseases in Nude Mice After Reconstitution of T Cell Function by Rat Fetal Thymus Graft", by Taguchi et al., in *J. Exp. Med.*, vol. 164, pp. 62–71, (Jul., 1986).

"Long–Term Human Hematopoiesis in the SCID–hu Mouse", by Namikawa et al., in *J. Exp. Med.*, vol. 172, pp. 1055–1063 (Oct., 1990).

"The SCID–hu Mouse: Murine Model for the Analysis of Human Hematolymphoid Differentiation and Function", by McCune et al., in *Science*, vol. 241, pp. 1632–1639 (Sep. 23, 1988).

"Transfer of a Functional Human Immune System to Mice with Severe Combined Immunodeficiency", by Mosier et al., in *Nature*, vol. 335, pp. 256–259 (Sep. 1988).

*Primary Examiner*—Karen M. Hauda
*Attorney, Agent, or Firm*—Amster, Rothstein & Ebenstein

[57] ABSTRACT

This invention is directed to a chimeric mouse capable of mounting murine cellular and humoral immune response, where the chimeric mouse is tolerant of human tissue implanted therein. The chimeric mouse of this invention is capable of developing murine T cells and producing murine IgG antibodies, which T cells and antibodies are tolerant of the human tissue implanted in the mouse. This allows for the challenge of the vaccinated mouse with human-specific pathogens and determining the capacity of the vaccine to protect the cells in the implanted tissue from infection. This invention is also directed to a method for the development of the chimeric mouse, as well as to the use of the chimeric mouse for the screening of vaccines for human-specific pathogens.

3 Claims, 11 Drawing Sheets

CHIMERIC MOUSE FOR HUMAN AND MOUSE IMMUNE SYSTEMS

This application is a divisional of U.S. patent application Ser. No. 08/739,281, filed Oct. 29, 1996, issued as U.S. Pat. No. 5,811,635; which is a continuation of Ser. No. 08/309,563, filed Sep. 20, 1994, now abandoned; which is a continuation of Ser. No. 07/924,348, filed Aug. 3, 1992, now abandoned.

STATEMENT OF GOVERNMENT INTEREST

This invention was made with government support under NIH Grant Nos. NIH AI-27741 and NIH AI-2067. The government has certain rights in this invention.

FIELD OF THE INVENTION

This invention is directed to the development of a mouse chimeric for both the human and mouse immune systems. The chimeric mouse of this invention has a reconstituted murine immune system, including both humoral immune response and cellular immune response. Specifically, the chimeric mouse of this invention is capable of developing murine T cells, as well as producing murine IgG antibody. In addition, the chimeric mouse of this invention is capable of tolerating human tissue, allowing for the maturation and function of implanted human tissue, including the maturation of human T cells. The chimeric mouse of this invention mounts primary and secondary murine immune responses to specific antigens.

BACKGROUND OF THE INVENTION

Vaccines comprise special preparations of antigenic materials that can be used to stimulate development of antibodies (humoral response) and T cell activity (cellular response), thereby conferring active immunity against a specific disease. Typically, vaccines are produced by culturing bacteria or viruses under conditions that lead to a loss of their virulence, but not of their antigenic nature. Some vaccines consist of specially treated toxins or of dead bacteria that are still antigenic. Live but weakened organisms are also used as vaccines. The immunization of humans or animals with vaccines produces active immunity, i.e., the stimulation of the body to produce its own antibodies.

Because the preparation of new vaccines may prove to be toxic or detrimental to persons immunized with said vaccines, it is desirable to immunize animals with new vaccines in order to determine whether the vaccines are both safe and effective in eliciting humoral antibody response. Although a vaccine may elicit a humoral and cellular response, that immune response may not be effective in protecting the animal from infection. Therefore, to demonstrate the effectiveness of a vaccine, the vaccinated animal should be challenged with the infectious agent. However, this is difficult because the pathogens that the vaccine is designed to protect against may be specific for humans and, therefore, the capacity of the vaccine to protect the animal from infection cannot be determined. Hence, it is desirable to develop an animal system wherein human vaccines may be tested for their abilities to elicit an animal antibody immune response that protects human tissue from infection.

In an unsuccessful attempt to create such animal systems, mice have been implanted with human fetal liver, hematopoietic cells, human fetal thymus and human fetal lymph node. See "The SCID-hu Mouse; Murine Model for the Analysis of Human Hematolymphoid Differentiation and Function", by McCune et al., in *Science*, Vol. 241, pages 1632–1639 (Sep. 23, 1988), wherein a chimeric mouse was created by implanting human fetal liver hematopoietic cells, fetal thymus and fetal lymph node into SCID mice in an attempt to create a chimeric mouse capable of responding to vaccines with both murine and human cellular immune response and humoral immune response.

The chimeric mouse developed by McCune et al. produced only transient human T cells. The McCune mouse did not produce any murine T cells, and hence the immunodeficient SCID mouse did not have its murine T cell function restored after implantation with human fetal tissue. Moreover, the mouse produced by McCune et al. showed no primary human immune response, and was not capable of any significant human or murine immune response.

Namikawa et al., in "Long-Term Human Hematopoiesis in the SCID-hu Mouse", *J. Exp. Med.*, Vol. 172, pages 1055–1063 (October, 1990), also attempted to produce a chimeric mouse capable of both murine and human cell mediated immune response and humoral immune response by implanting human fetal thymus and fetal liver into immunodeficient SCID mice. However, the resulting Namikawa et al. mouse did not have a reconstituted murine immune system. Specifically, there were no murine T cells found in the mouse, indicating that murine T cell function was not restored. In addition, the Namikawa et al. chimeric mouse produced only transient human T cells. Finally, there was no primary human immune response in the Namikawa et al. mouse, nor was there any significant human or murine immune response.

Similarly, Mosier et al., in "Transfer of a Functional Human Immune System to Mice with Severe Combined Immunodeficiency", in *Nature*, Vol. 335, pages 256–259 (September, 1988), attempted to produce a chimeric mouse with a reconstituted murine immune system capable of mounting human antibody response to vaccinations with antigens such as tetanus toxoid. These mice were produced by injecting human peripheral blood leukocytes (PBL) into immunodeficient SCID mice to produce SCID-PBL mice. The chimeric mouse produced by Mosier et al. did show a low level of human immune response to the antigen tetanus toxoid. This probably reflected a secondary response to tetanus by the human PBL obtained from a donor already immunized with tetanus. However, the amount of human T cells in said mice decreased over a short period of time, and there was no human T cell maturation in such mice. In addition, the murine immune system was not reconstituted. As a result, the chimeric mouse produced by Mosier et al. was not capable of any significant murine and human primary immune response.

Finally, Taguchi et al., in "Development of Multiple Organ-Localized Autoimmune Diseases in Nude Mice After Reconstitution of T Cell Function by Rat Fetal Thymus Graft", in *J. Exp. Med.*, Vol. 164, pages 60–71 (July, 1986), attempted to restore the murine immune system by implanting rat thymus into congenitally athymic nude mice. The chimeric mouse produced by Taguchi et al. produced very few rat lymphoid cells. In addition, murine T cell function was only somewhat restored. Further, in response to the implantation of rat thymus, the chimeric mouse developed autoantibodies and autoimmune diseases over a period of time.

Hence, a need exists for an animal which has a reconstituted animal immune system, contains target tissue susceptible to infection with human-specific pathogens, and is capable of mounting an immune response to human pathogens. Such an animal will allow researchers to determine whether a vaccine will cause an animal immune response which serves to protect human tissue in said animal.

Therefore, it is an object of this invention to produce an animal which is chimeric, and capable of both human and animal immune response, including cell mediated immune response and humoral immune response, said animal also containing target tissue for infection with human-specific pathogens.

It is another object of this invention to provide an animal system capable of responding to antigens by producing both human and murine T cells.

It is a further object of this invention to provide an animal system capable of responding to human-specific antigens by producing antigen-specific antibodies.

It is another object of this invention to provide a method of producing an animal system capable of both animal and human cellular and humoral immune response.

It is still another object of this invention to provide an animal system capable of responding to vaccines by the production of human and animal T cells and animal antibodies.

It is yet another object of this invention to provide a chimeric animal system for use in the production of both monoclonal and polyclonal antibodies.

It is a further object of this invention to provide an animal system useful for the study of human autoimmune diseases, human-specific pathogens and tissue-specific pathology.

SUMMARY OF THE INVENTION

This invention is directed to a chimeric mouse which has a reconstituted murine immune system and is tolerant of human tissue. The chimeric mouse of this invention allows for the concomitant maturation of both murine and human T cells, and produces murine antibodies. In addition, the chimeric mouse of this invention mounts a humoral response to new antigens, thereby indicating that murine T cells maturing in human thymus can interact with murine B cells and exhibit a primary and secondary response.

This invention is further directed to the production of said chimeric mouse. Said mouse is produced by implanting both thymus and liver obtained from a single fetus under the kidney capsules of a congenital athymic mouse such as the bg/nu/xid (BNX) mouse. The bg/nu/xid mouse has reduced NK cells and reduced LAK cell activity, and does not have a thymus. Because the chimeric mouse of this invention provides for a reconstituted murine immune system as well as allowing for the maturation of human T cells, the chimeric mouse of this invention may be used for the screening of human-specific vaccines and chemotherapeutic agents, the production of monoclonal and polyclonal antibodies, and the study of autoimmune diseases, human-specific pathogens and tissue-specific pathology.

BRIEF DESCRIPTION OF THE DRAWINGS

The above brief description, as well as further objects and features of the present invention, will be more fully understood by reference to the following detailed description of the presently preferred albeit illustrative, embodiment of the present invention when taken in conjunction with the accompanying drawings wherein:

FIGS. 1A–D:

FIG. 2 represents the distribution of the human leukocyte common antigen CD45 (A and B), the distribution of murine T cell CD8 (C and D), the distribution of murine T cell CD4 (E and F) and murine Ia (G) as shown by immunohistochemical staining in the human thymic implant.

DETAILED DESCRIPTION OF THE INVENTION

Figure 1:
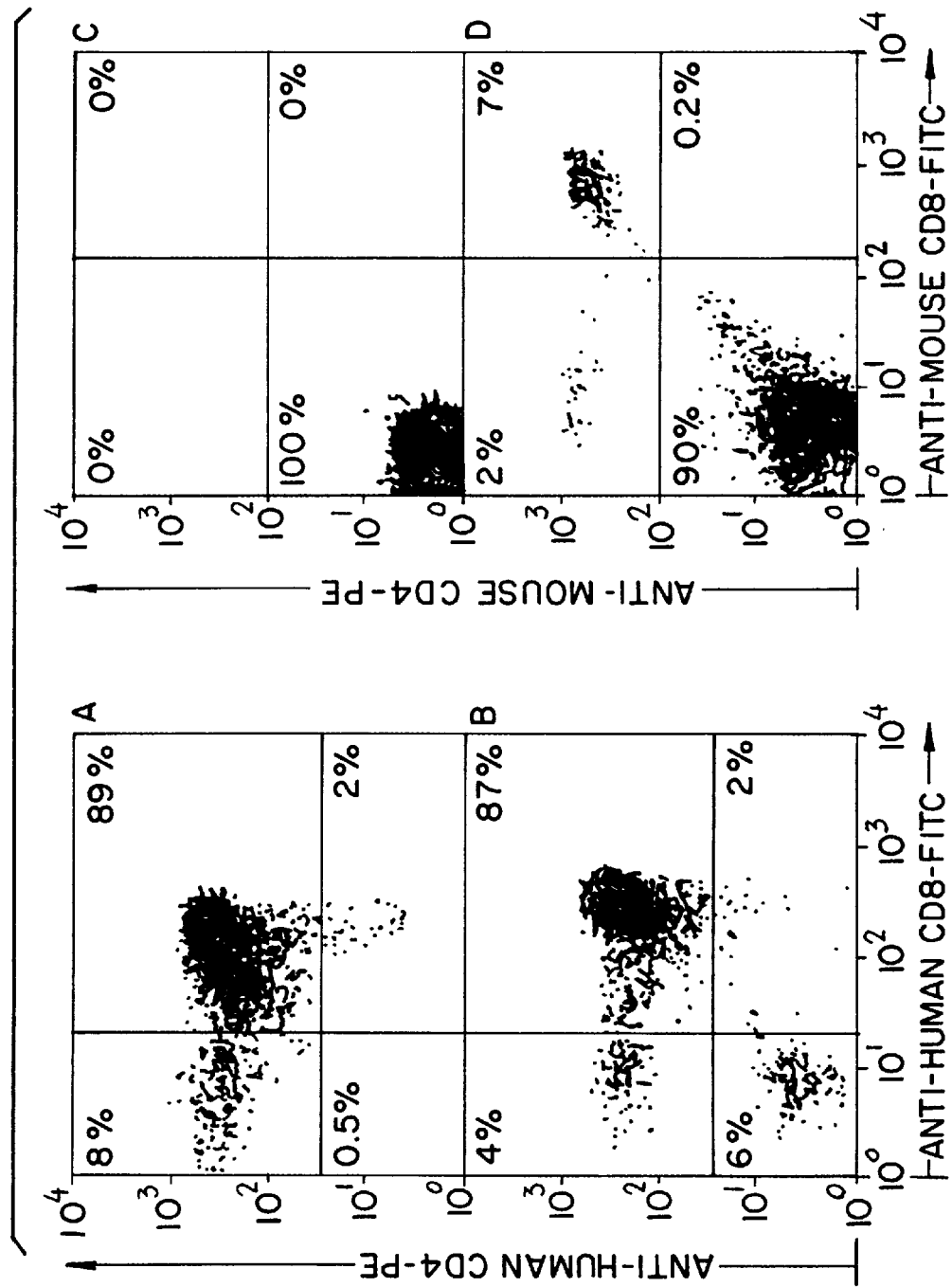
FIG. 1 represents flow cytometric analysis of the maturation of human T cells in implanted human thymic tissue, as shown by the count of single positive and double positive lymphocytes for human T cells CD4 and CD8 (A and B). The presence of murine T cells CD4 and CD8 are shown as expressed on lymphocytes (C and D).

Nude mice, beige mice and xid mice have been crossed in order to create the bg/nu/xid strain of mice, which mice are immunodeficient, with a greater tolerance for xenografts. bg/nu/xid mice have reduced NK cell activity and reduced LAK cell activity. The reduction in NK cell activity and LAK cell activity, as well as the lack of a thymus, allow bg/nu/xid mice to accept implants of foreign tissues more readily.

Both bg/nu/xid and SCID mice 6–8 weeks old were anesthetized with 80 mg/kg pentobarbital. Thymus and liver were obtained from a single human fetus with a gestational age of 17 weeks, dissected into 1 mm$^3$ pieces, and implanted together by sterile techniques with a 16 gauge trocar under the left kidney capsules within 8 hours of availability. Fetal liver tissue was implanted with the thymic tissue to provide a source of human precursor cells that are required for the continued presence of human T cells in the thymic graft. Following surgery, the mice were started on trimethoprim/sulfamethoxazole antibiotic (TMS, Schein Pharmaceutical Inc., Port Washington, N.Y.) and housed in bonnetted isolator cages (Lab Products, Inc., Federalsburg, Md.) in an environment that was monitored for mouse pathogens. The mice were sacrificed by lethal ether inhalation three months later for analysis. The hu-thy/liv implants, spleens and lymph nodes were removed, dissected free of all mouse tissue, gently teased into a single cell suspension, filtered through a stainless steel mesh and then washed three times in ice cold PBS containing 1% BSA and 0.1% NaN$_3$ (PBS/BSA/azide). The dissected implanted tissue was found to have increased in size from 1 mm$^3$ to about 5×5×10 mm. Microscopic examination revealed that the implanted tissue had well demarcated cortical and medullary regions which closely resembled those of normal human thymus. In addition, there was no histological evidence of graft rejection.

In order to determine whether there was maturation of human T cells in the implanted human thymic tissue, two-color flow cytometric analysis was performed on both the fetal liver and thymus-implanted bg/nu/xid mice (BNX-hu) and also on the SCID mice similarly implanted with human fetal and thymus tissues (SCID-hu mice). The lymphocytes from the implants in SCID-hu mice and BNX-hu mice were simultaneously stained with either phycoerythritin-conjugated mouse monoclonal antibody to human CD4 (Leu 3a, Becton Dickenson, Mountainview, Calif.) and fluorescein isothiocyanate-conjugated mouse monoclonal antibody to human CD8 (Leu 2a, Becton Dickenson, Mountainview, Calif.) (see panels A and B of FIG. 1), or with phycoerythritin-conjugated rat monoclonal antibody to mouse CD4 (L3T4, Pharmingen, San Francisco, Calif.) and fluorescein isothiocyanate-conjugated rat monoclonal antibody to mouse CD8 (Ly-2, Pharmingen) (see panels C and D of FIG. 1), and analyzed by flow cytometry on a FACScan (Becton, Dickenson). Founder homozygous CB17 scid/scid (SCID) mice delivered by caesarean section were bred by Albert Einstein College of Medicine of Yeshiva University in pathogen-free breeding colonies according to institutional guidelines. The mice were obtained in sterile isolators without prophylactic antibiotic treatment. Homozygous bg/nu/xid mice were obtained from NCI (Frederick, M.D.).

$0.5 \times 10^5$ thymocytes were incubated with the indicated antibodies for thirty minutes at 4° C. and then washed and fixed in 1% paraformaldehyde in PBS for twelve hours. The antibodies were used at saturating conditions and showed no species cross-reactivity. Prior to analysis, cells were washed and resuspended in buffer (PBS/BSA/azide) and, after non-viable cells and unlysed red blood cells were gated out based on their forward and side scatter profiles, 20,000 events per sample were recorded ungated on FACScan cell analyzer with LYSIS-II software (Becton, Dickenson). Analysis was performed on lymphocytes that were gated on the basis of forward and side scatter profile to correspond to gates set to include both control human (from healthy adult volunteer) and mouse (from healthy CB.17 mice) lymphocytes. Following compensation for PE vs. FITC emission based on a single and double staining of positive and negative control samples and analysis of appropriate isotype controls, quadrants were set in each experiment. The percentage of CD4+ CD8, CD4+CD8−, CD4−CD8+ and CD4−CD8− cells were indicated in the appropriate quadrant. The results are shown in FIG. 1, and represent results obtained following the analysis of implants from four BNX-hu. and four SCID-hu mice.

Over 85% of the human lymphocytes from the SCID-hu and BNX-hu mice were double positive for CD4 and CD8, and the remainder were single positive for either CD4 or CD8. FIG. 1A shows that the SCID-hu mouse had a mixed population of single positive and double positive lymphocytes with the majority of cells being double positive for human CD4 and CD8. FIG. 1B shows that the BNX-hu mouse also had a mixed population of single positive and double positive lymphocytes with the majority of cells being double positive for human CD4 and CD8. Both the SCID-hu and BNX-hu mice showed phenotypic maturation of human T cells occurring in the human thymic tissue, comparable to that which occurs in normal human thymus. However, a significant number of the lymphocytes in the BNX-hu implant were negative for human CD4 and CD8. Hence, there is a disparity between the number of human double negative cells detected in the BNX-hu implant and the number detected in the SCID-hu implant. This is accounted for by the presence of murine T cells in the BNX-hu implant, but not in the SCID-hu implant.

As shown in FIG. 1C, there were no murine T cells observed in a SCID-hu implant. In contrast, as shown in FIG. 1D, 9.2% of the cells detected in the BNX-hu implant were murine T cells that were either single positive for CD4 or CD8 (2.2%), or double positive for CD4 and CD8 (7.0%).

Figure 2A:
FIGS. 2A–G.
Figure 2B:
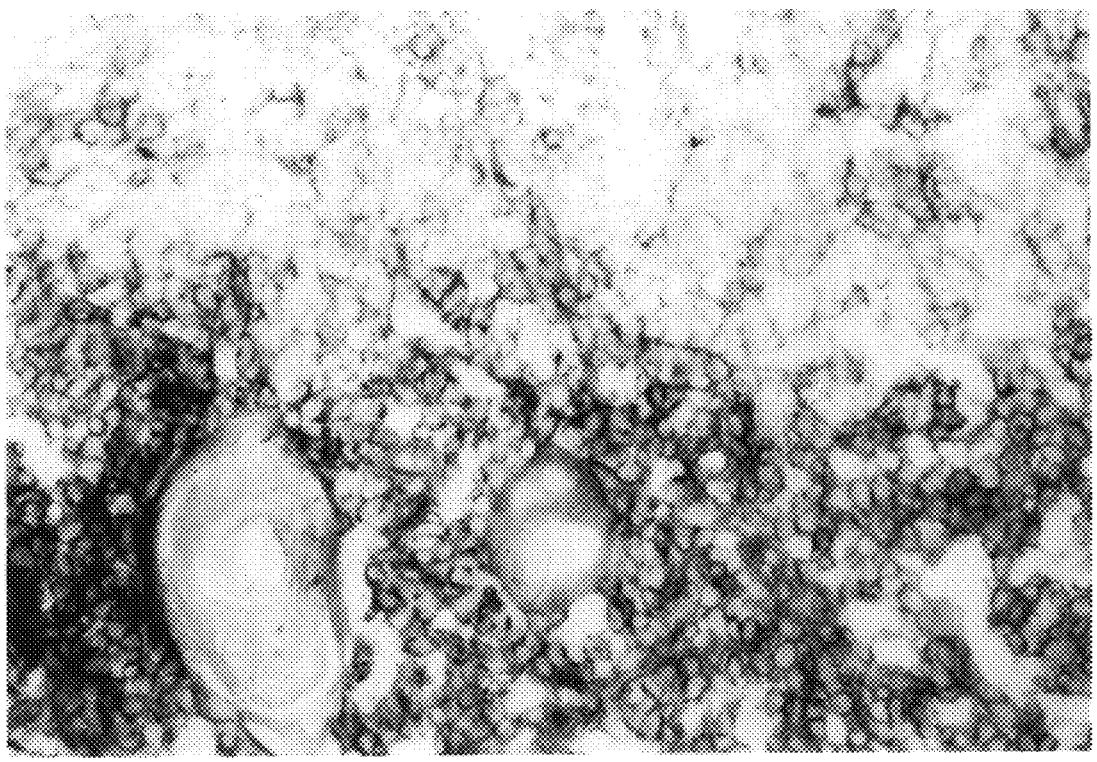
Figure 2C:
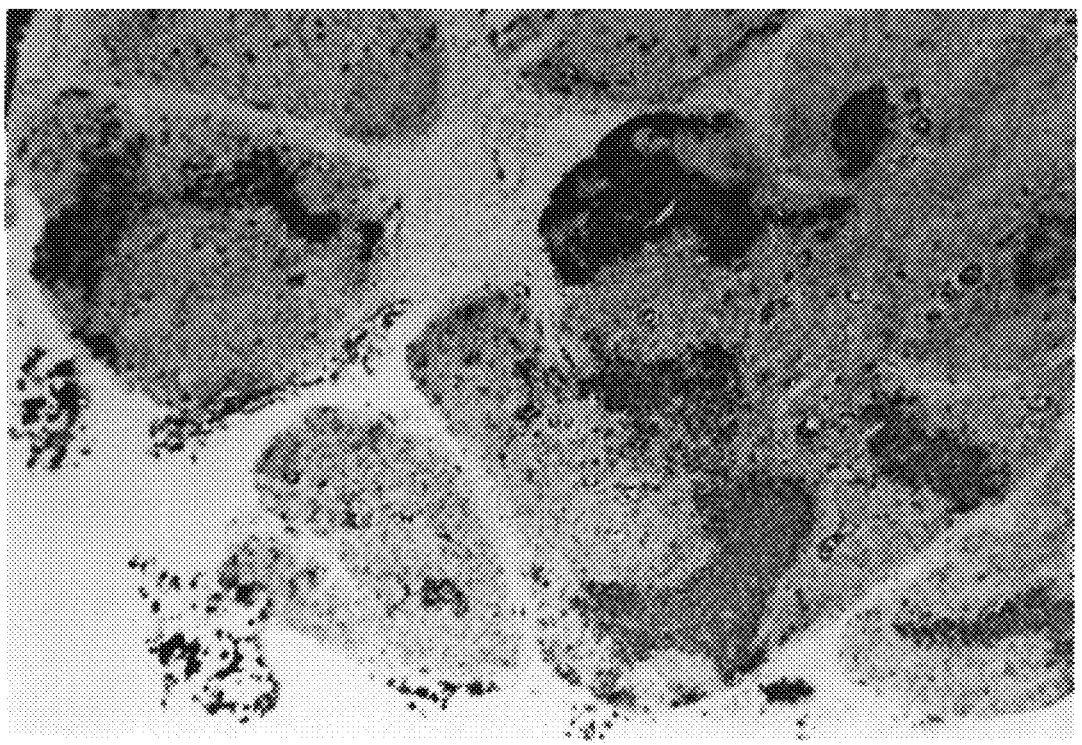
Figure 2D:
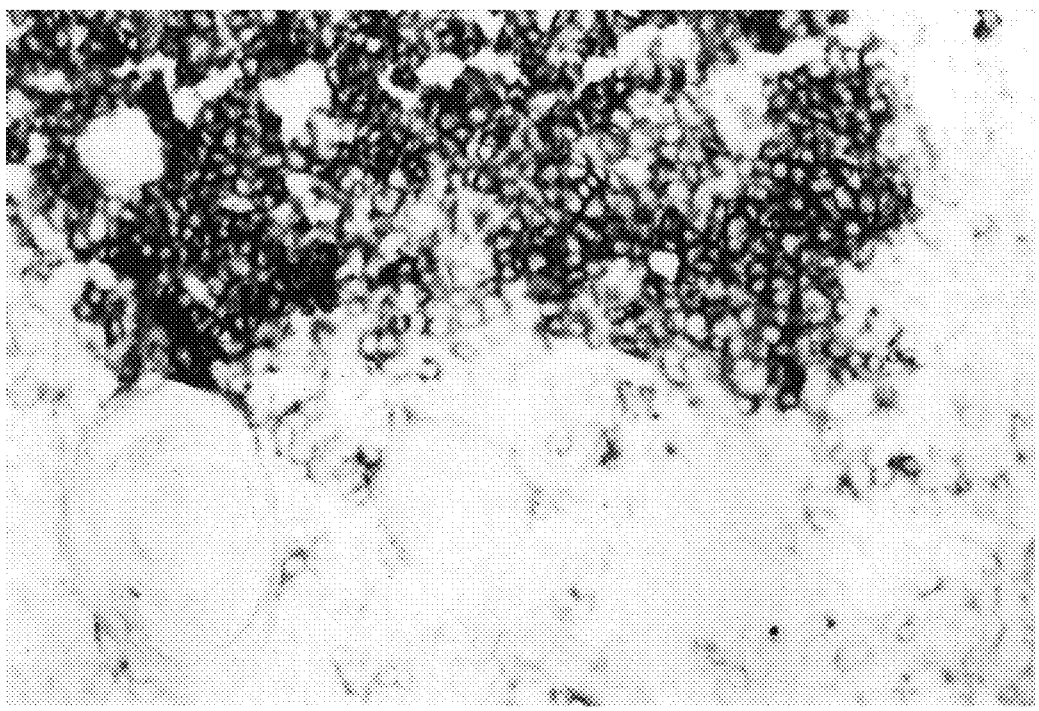

Immunohistochemical staining was performed in order to determine the distribution of the human leukocyte common antigen CD45, as well as the distribution of murine T cell CD8 and murine T cell CD4. Photomicrographs of immunohistochemical stained serial sections of the BNX-hu implants were evaluated for expression of human CD45 (FIGS. 2A and 2B), murine CD8 (FIGS. 2C and 2D), murine CD4 (FIGS. 2E and 2F) and murine Ia (FIG. 2G). FIGS. A, C and E are shown at 100x magnification. FIGS. B, D, F and G are shown at 400x magnification. After lethal ether inhalation, one-third of the implants were immediately dissected, imbedded in OCT, snap frozen in liquid nitrogen and then stored at −70° C. Serial frozen sections (5 μm) of the hu-thy/liv implants were mounted on poly-L-lysine (Sigma, St. Louis, Mo.) coated slides and fixed in cold acetone at 40° C. for 10 minutes. The sections were incubated with either biotin-conjugated mouse antibodies to human CD45, rat antibody to mouse CD4, rat antibody to mouse CD8 overnight at 4° C. or rat antibody to mouse Ia. Sections to which primary rat monoclonal antibodies had been applied were then incubated with biotinylated-rabbit antibodies (mouse-adsorbed) to rat IgG (Vector Laboratories, Burlingame, Calif.) for 30 minutes. The sections were then stained by the avidin-biotin-peroxidase complex (ABC) method using an ABC kit (Vector Laboratories). Each step was followed by two washes in Tris-buffered saline, pH 7.4, and all of the antibodies used did not exhibit any species cross-reactivity.

Figure 2E:
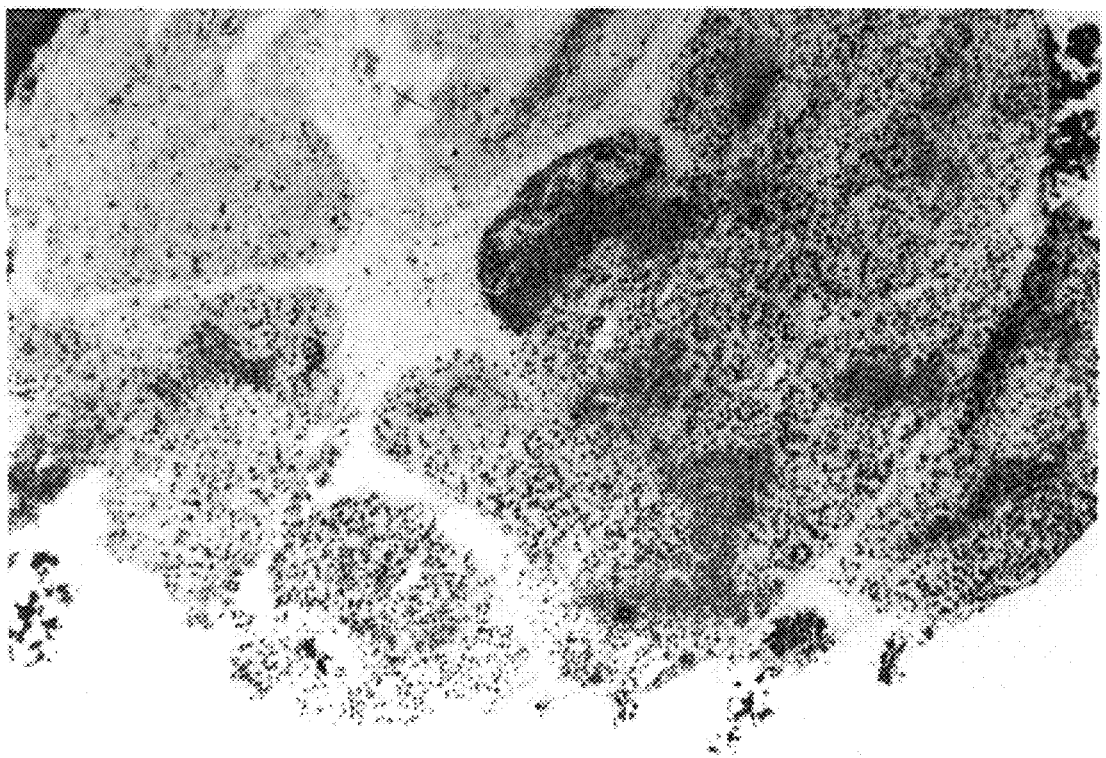
Figure 2F:
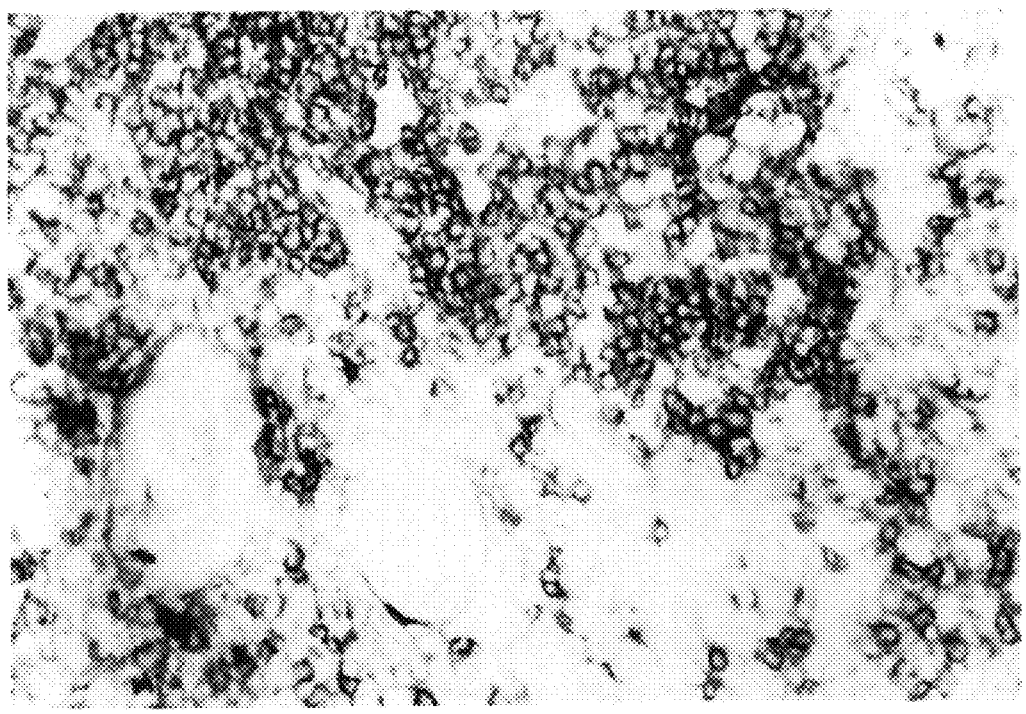
Figure 2G:
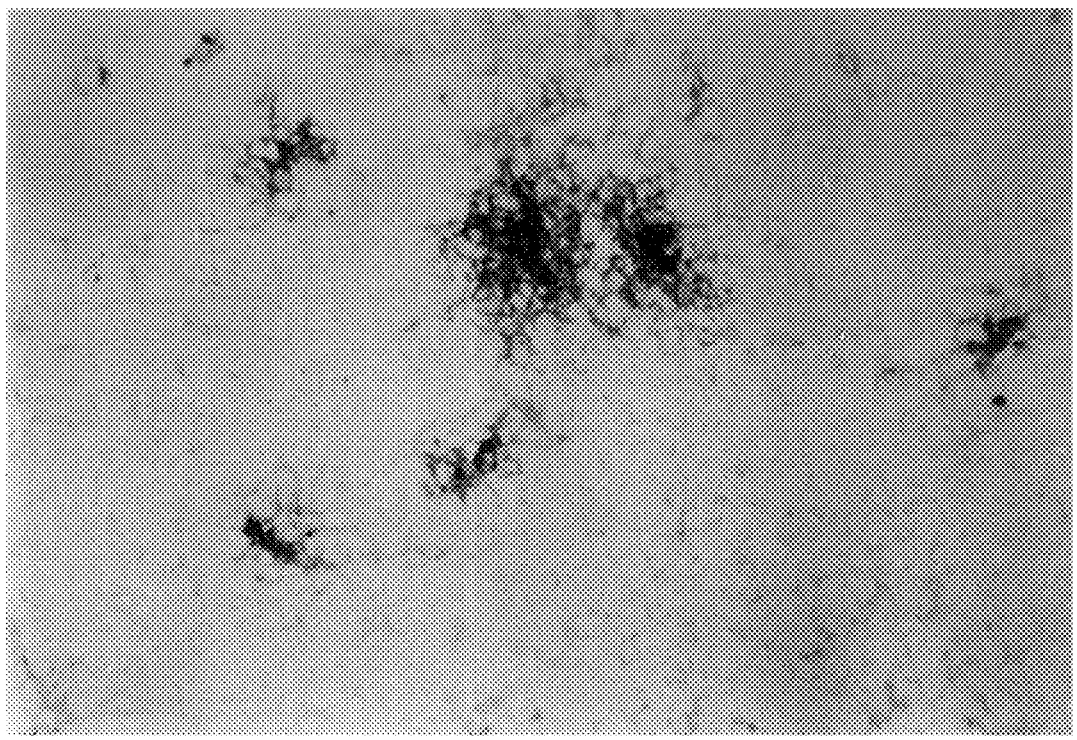

Although the majority of the cells present in the BNX-hu implanted thymus were positive for human CD45, there were clusters of cells in some thymic lobes that did not express human CD45 (FIGS. 2A and 2B), but rather expressed both murine CD8 (FIGS. 2C and 2D) and murine CD4 (FIGS. 2E and 2F). While most murine CD8 cells in the implant were confined to the human CD45 negative and murine CD4 positive regions, low numbers of murine CD4 positive cells were also found disbursed throughout the implant. In contrast, immunohistochemical staining of the SCID-hu implant did not reveal murine CD4 or CD8 positive cells. Denditric appearing cells that were murine Ia positive were scattered in the medulla and cortex of the BNX-hu (FIG. 2G) and SCID-hu implants.

Expression of murine CD4 and CD8 T cells on lymphocytes in blood, spleen and lymph nodes was measured as a means of detecting the degree of reconstitution of murine T cells. Table I shows the flow cytometric analysis of blood, lymph node and spleen of BNX, BNX-hu and BALB/c mice three months after implantation with human fetal thymus and liver. After dead cells were gated out, 20,000 absolute events were acquired and lymphocyte gates were set. The mean number of events occurring within the lymphocyte gates and the percentage of cells within the lymphocyte gates expressing murine CD4 or murine CD8 are given. 500 μl blood obtained from the retro-orbital sinus were collected in 500 μl of PBS containing 3 mg/ml EDTA and 1 μg//ml NaN₃. Spleen and lymph node (LN) was dissected clear of any connective tissue, minced into a single cell suspension and red blood cells were lysed in Tris-buffered ammonium chloride. The results shown are mean values obtained from one BNX mouse, two BNX-hu mice three months after implantation and one BALB/c mouse. The BNX-hu mice implant displayed a significant degree of restoration of CD4 or CD8-expressing murine lymphocytes in the peripheral blood, spleen and lymph nodes. In contrast, the SCID-hu mice implant did not display a significant degree of restoration (data not shown).

TABLE I

Flow Cytometric Analysis of Blood, Lymph Node and Spleen of BNX, BNX-hu and BALB/c Mice.

|  | Blood | | | Lymph Node | | | Spleen | | |
| --- | --- | --- | --- | --- | --- | --- | --- | --- | --- |
|  | BNX | BNX-hu | BALB/c | BNX | BNX-hu | BALB/c | BNX | BNX-hu | BALB/c |
| Lymphocytes | 7,000 | 10,250 | 10,700 | 380 | 8,595 | 18,100 | 650 | 8.750 | 16,300 |
| CD4 | 2.0% | 9.0% | 34.0% | 8.0% | 34.5% | 36.6% | 9.5% | 16.0% | 14.5% |
| CD8 | 1.3% | 12.1% | 18.0% | 5.0% | 7.9% | 16.8% | 4.9% | 7.2% | 8.0% |

In order to determine whether correction of the T cell defect restored BNX-hu murine B cell function, the concentration of mouse serum IgG subclasses was determined. This was performed by radioimmunodiffusion (RID) assay, and was performed on serum of six SCID-hu mice before and six weeks after implantation, six BNX-hu mice before and six weeks after implantation, and two BNX mice housed together with the BNX-hu mice. An aliquot of 5 $\mu$l of serum was applied to IgG subclass-specific RID plates for the quantification of mouse IgG1, IgG2A, IgG2B and IgG3. After incubation for 24 hours at 37° C., the plates were read according to the manufacturer's protocol and proper assay conditions were insured by the inclusion of internal standards on every plate. Human IgG did not cross react with the RID plates used. The results are shown in Table II below, and are shown as mean ± SEM.

TABLE II

Quantitation of Mouse IgG Subclass Antibodies in BNX and pre- and post-implant BNX-hu and SCID-hu mice.

|  | IgG1 (mg/ml) | IgG2a (mg/ml) | (IgG2b (mg/ml) | IgG3 (mg/ml) |
| --- | --- | --- | --- | --- |
| BNX | 0.20 ± 0 | 0 | 0 | 0 |
| BNX-hu (pre-implant) | 0.23 ± 0.06 | 0 | 0 | 0 |
| BNX-hu (post-implant) | 22.32 ± 4.16 | 12.83 ± 3.27 | 2.02 ± 0.33 | 1.50 ± 0.06 |
| SCID-hu (pre-implant) | 0 | 0 | 0 | 0 |
| SCID-hu (post-implant) | 0.04 ± 0.04 | 0 | 0 | 0 |

In contrast to the markedly reduced levels of all IgG subclasses observed in sera from age-matched control BNX mice and pre-implant BNX-hu mice, all mouse IgG subclasses were detected at either normal or elevated levels in the post-implant BNX-hu mice. The concentration of mouse IgG in the serum of SCID-hu mice was not affected by implantation of human fetal thymic and liver tissue.

Figure 3:
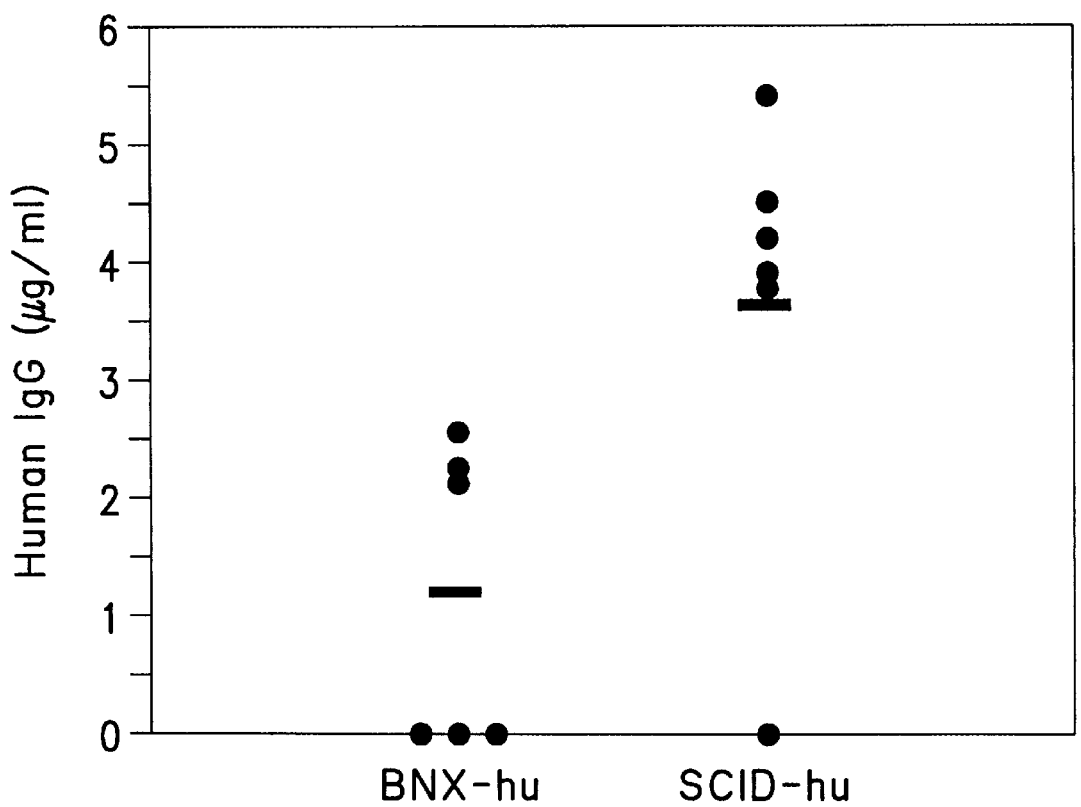
FIG. 3 represents the concentration of human IgG in BNX-hu and SCID-hu mice.

Since human T cells and IgG can be detected in the blood of SCID-hu mice, the degree of reconstitution of BNX-hu mice with the human immune system was compared to that observed in SCID-hu mice. As shown in Table III below, although cells positive for human CD4 and CD8 were detected in the peripheral blood of both SCID-hu and BNX-hu mice, a higher percentage of human CD4 positive cells was detected in SCID-hu mice than in BNX-hu mice (p<0.05). Six weeks after implantation, the concentration of human IgG present in the serum of BNX-hu and SCID-hu mice was determined using an ELISA assay specific for human IgG. As shown in FIG. 3, low quantities of human IgG were detected in the sera from both the SCID-hu mice and the BNX-hu mice. More human IgG was present in SCID-hu mice than in BNX-hu mice (p<0.05). These results indicate that although some degree of reconstitution of the human immune system was occurring in BNX-hu mice, more reconstitution of the human immune system occurred in SCID-hu mice.

TABLE III

Percentage of Human CD4 and CD8 Expressing Leukocytes in the Peripheral Blood of SCID-hu and BNX-hu Mice

|  | Human CD4 | Human CD8 |
| --- | --- | --- |
| SCID | 0 ± 0 | 0 ± 0 |
| SCID-hu | 3.98 ± 0.24 | 0.10 ± 0.04 |
| BNX | 0 ± 0 | 0 ± 0 |
| BNX-hu | 0.17 ± .05 | 0.08 ± 0.03 |

B cell function was further evaluated by examining whether the BNX-hu mice could mount an antigen-specific humoral immune response. Animals were primed by intraperitoneal injection with 100 $\mu$g KLH (Pierce, Rockford, Ill.) or 20 $\mu$g of recombinant gp120 (NIH) in complete Freund's adjuvant (Difco Lab, Detroit, Mich.) and boosted one month later with 100 $\mu$g KLH or 20 $\mu$g of recombinant gp120 (NIH) in incomplete Freund's adjuvant. KLH-specific or gp120-specific murine IgG antibodies present in BNX-hu and bg/nu/xid mice were detected by ELISA. In order to perform the ELISA, microtiter plates (Corning, N.Y.) were coated with 10 $\mu$g/ml KLH or 1 $\mu$g/ml of gp120 in 100 mM NaHCO$_3$ pH 9.6, overnight at 4° C. and blocked for 1 hour at room temperature with PBS containing 1% BSA and 1% goat serum. Serum samples were added as the indicated dilution for 12 hours at 4° C. The plates were extensively washed and then incubated with alkaline phosphatase-conjugated goat anti-mouse IgG (Jackson Immunolabs, West Grove, Pa.) for 2 hours at room temperature. The plates were washed, substrate solution (P-nitrophenyl phosphate, Sigma) was added and adsorbance at 405 nm was measured with an automated spectrophotometer (Titertek Multiscan, Flow Laboratories, McLean, Va.).

Figure 4:
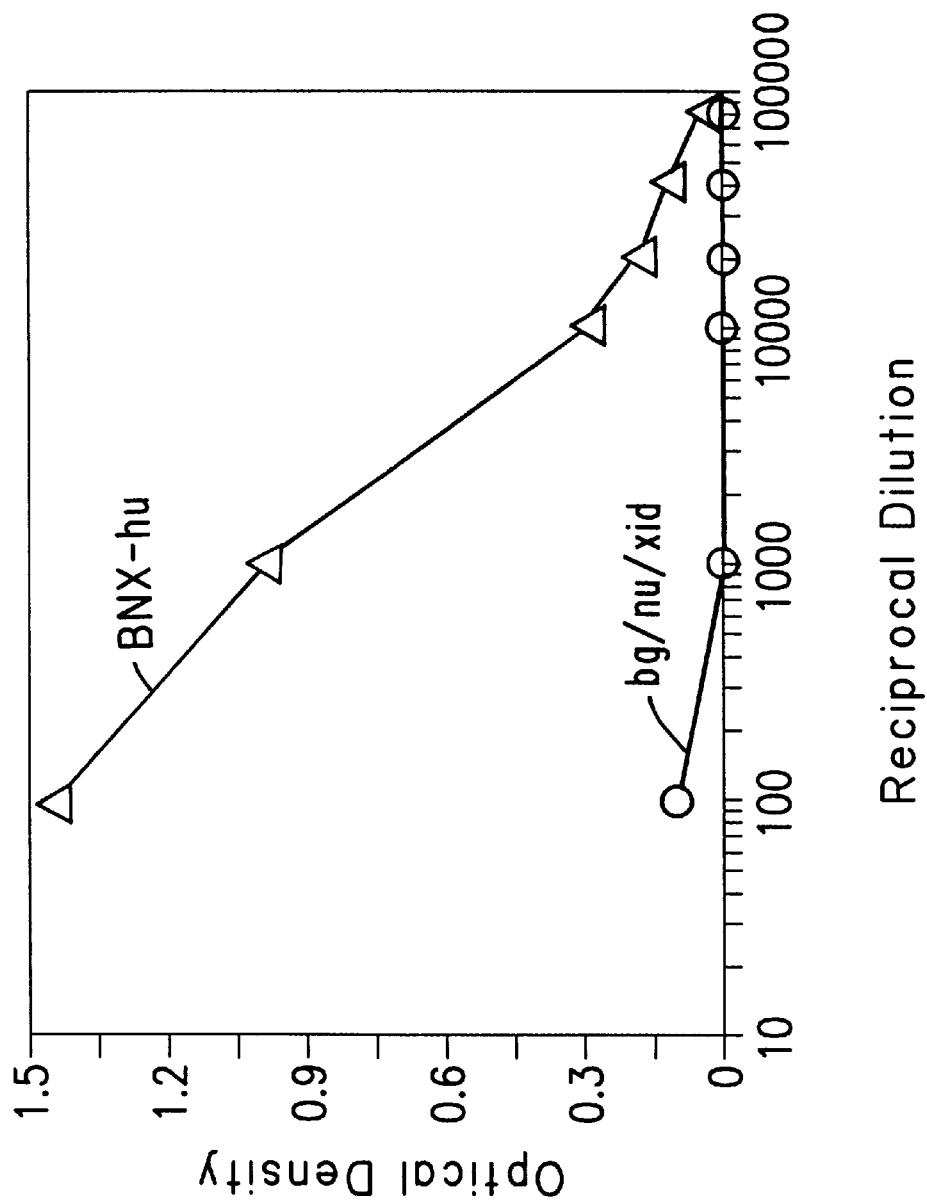
FIG. 4 represents the antigen-specific humoral response mounted after immunization with the antigen KLH.
Figure 5:
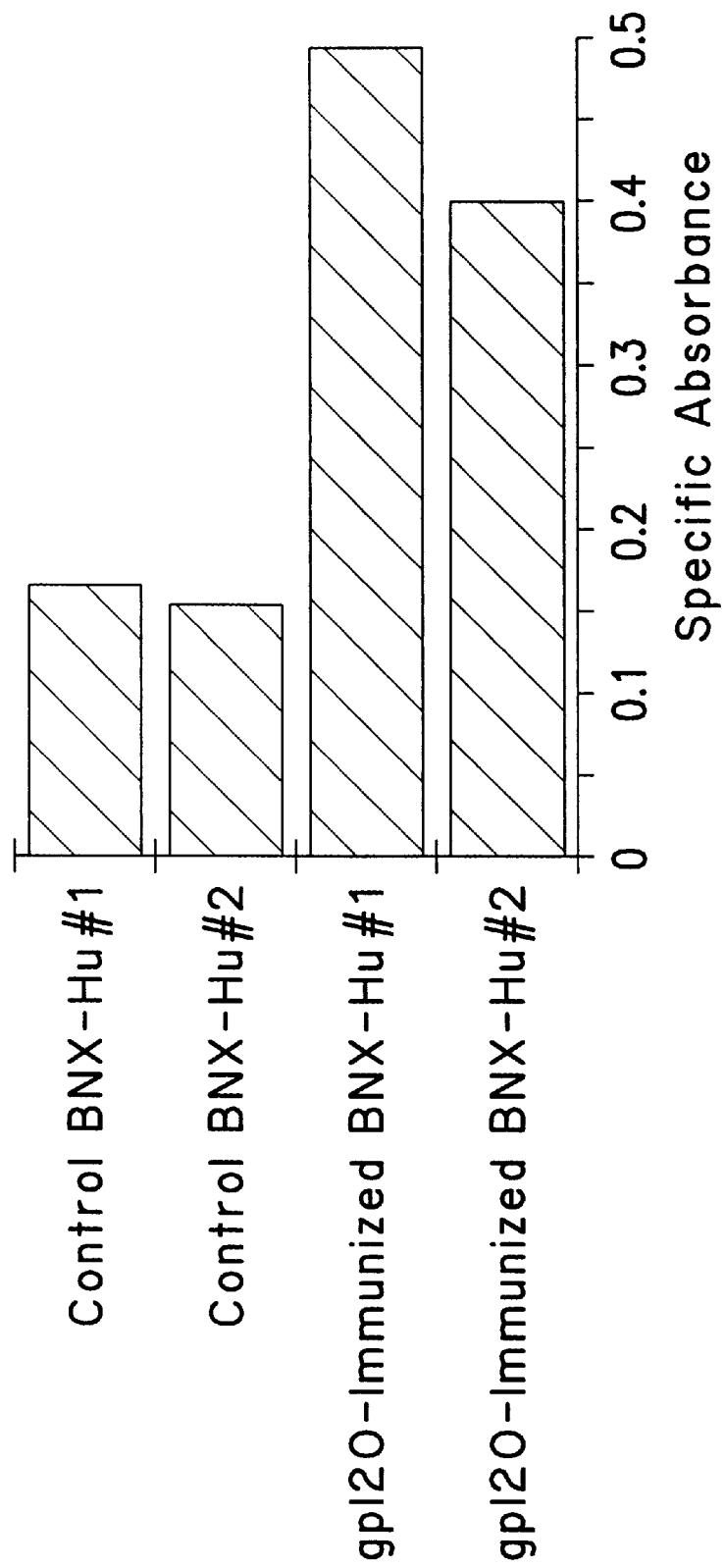
FIG. 5 represents the antigen-specific humoral response mounted after immunization with the antigen gp120, the capsular HIV-1 protein.

FIG. 4 shows IgG antibody response to KLH. Values given are the mean values of quadruplicate determinations for each reciprocal dilution of mouse serum assayed, and were normalized for IgG concentration. In contrast to the bg/nu/xid mice in which a humoral response to KLH was not detected, BNX-hu mice developed a significant murine IgG response to KLH. FIG. 5 shows mouse IgG antibody response to gp120. Valves given are the mean values of duplicate samples. gp120 is the antigen used in several candidate vaccines for HIV-1. Despite the fact that low levels of human IgG were detected in BNX-hu serum, no human IgG antibodies to KLH were detected.

The results presented herein demonstrate that the thymic defect present in bg/nu/xid mice can be corrected by the implantation of human fetal thymus and liver. The cellular and humoral reconstitution was not due to environmental factors, as comparable reconstitution was not observed in age-matched bg/nu/xid mice housed together with the BNX-hu for the entire period of the experiment. The concurrent presence of populations of murine and human double positive and single positive T cells in the implant indicated that active maturation of both human and murine T cells was occurring in the human thymus. This is in contrast to what occurred in rat thymic tissue implanted in nude mice, wherein few rat lymphoid cells were observed. This is probably because co-implantation of fetal liver provides a continuous source of human pre-T cells for maturation in the thymus. Although significant numbers of human T cells (up to 5.4%) were detected in the blood. and lymphoid organs of the SCID-hu mice, less than 1% of the lymphocytes in the peripheral blood and lymphoid tissues of the BNX-hu mice were human T cells. It is possible that this was due to the relative large number of murine T cells in the BNX-hu mice.

Although mouse T cells have been shown to traffic through rat thymic tissue implanted in nude mice, the maturational state was not delineated. The observation that the double positive murine T cells are clustered in discrete regions is highly suggestive of targeted homing and subsequent maturation of mouse pre-T cells in the implant, and not merely deposition of circulating double positive T cells that had differentiated extrathymically. In addition, whereas no double positive mouse T cells were detected in the peripheral blood, spleen, lymph nodes or thymic rudiments of BNX-hu mice by flow cytometry, over 75% of the murine T cell population in the implant consisted of double positive lymphocytes. Thus, CD4 and CD8 expression by murine T cells differentiating in xenogeneic thymic tissue is similar to that observed in normal murine thymus. Whether the developmentally regulated expression of the T cell receptor and other surface molecules by murine thymocytes maturing in the BNX-hu implant resembles that of the normal murine thymocyte ontogeny is currently being studied.

The maturation of murine T cells in human thymus permits a unique strategy for evaluating T cell maturation in an HIV-infected thymic environment. Because murine T cells are not susceptible to HIV infection, the consequences of HIV infection of human thymic cells on murine T cell maturation can be studied independently of the influence of their becoming infected with HIV. The presentation of HIV antigens to murine T cells undergoing maturation in the thymus may result in the negative selection of T cells expressing T cell receptors that recognize HIV antigens. This may have implications in understanding the effect of congenital HIV infection on maturation and clonal deletion of uninfected T cells in the thymus.

In addition, BNX-hu mice with a reconstituted autologous immune system that are tolerant of the continued presence of human T cells can be used as a new model for the evaluation of HIV vaccines. Since human thymic implants in BNX-hu mice could be productively infected with HIV, they can be used to evaluate the capacity of HIV vaccines to generate in vivo murine protective immune responses. Following immunization with an HIV antigen, such as gp120, the capacity of the resultant murine immune response to protect the thymic implant from HIV infection can then be assessed. It has been demonstrated that these mice develop a humoral response to gp120. Although the great majority of the elicited immune response in the BNX-hu model is that of murine origin and not of human origin, nevertheless, the BNX-hu mice mount a significant primary and secondary murine humoral response following immunization with antigen. Therefore, the BNX-hu mouse is a better model for evaluating HIV vaccines than other mouse-human chimeric models such as SCID-hu mice or SCID-PBL mice which have not been shown to mount significant primary immune responses of either human or murine origin. Similarly, lethally irradiated BALB/c mice transplanted with human bone marrow cells developed only low levels of human antibodies to DNP following immunization with DNP-KLH. In contrast, a murine model with a reconstituted immune system that is tolerant of a human thymic implant has been described herein. This model can be used in understanding the mechanisms of thymic maturation of T cells and in evaluating potential vaccines. In addition, the chimeric mouse of this invention can be used in the production of monoclonal and polyclonal antibodies, as well as in the study of autoimmune diseases, tissue-specific pathogenesis and human pathogens.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

What is claimed is:

1. A method of determining the effectiveness of a vaccine for inducing an active immune response in a mouse comprising:

(a) providing a BNX mouse implanted with both human fetal thymus tissue and human fetal liver tissue under the kidney capsule of said mouse, said mouse being capable of mounting murine cellular and humoral antibody responses, wherein said mouse does not reject the implanted human tissue;

(b) injecting said mouse with said vaccine and determining if said vaccine induces an active immune response in said mouse.

2. The method of claim 1, wherein said mouse is further challenged with a human pathogen and determining if said human tissue is protected from infection of said human pathogen.

3. The method of claim 1, wherein said BNX mouse is capable of developing murine T cells, producing murine IgG antibody and allows for the maturation of human T-cells.

* * * * *